United States Patent
Raghavan et al.

(10) Patent No.: US 10,621,305 B2
(45) Date of Patent: *Apr. 14, 2020

(54) WIRELESS MEDICAL ROOM CONTROL ARRANGEMENT FOR CONTROL OF A PLURALITY OF MEDICAL DEVICES

(71) Applicant: Stryker Corporation, Kalamazoo, MI (US)

(72) Inventors: Prabhu Raghavan, San Jose, CA (US); Travis Morgan, San Mateo, CA (US)

(73) Assignee: Stryker Corporation, Kalamazoo, MI (US)

(*) Notice: Subject to any disclaimer, the term of this patent is extended or adjusted under 35 U.S.C. 154(b) by 155 days.

This patent is subject to a terminal disclaimer.

(21) Appl. No.: 15/671,851

(22) Filed: Aug. 8, 2017

(65) Prior Publication Data

US 2017/0337340 A1 Nov. 23, 2017

Related U.S. Application Data

(63) Continuation of application No. 12/454,622, filed on May 20, 2009, now Pat. No. 9,740,826.

(Continued)

(51) Int. Cl.
*G06F 19/00* (2018.01)
*G16H 40/63* (2018.01)
*G16H 40/20* (2018.01)

(52) U.S. Cl.
CPC ......... *G06F 19/3418* (2013.01); *G16H 40/63* (2018.01); *G16H 40/20* (2018.01)

(58) Field of Classification Search
CPC ..... G06F 19/3418; G16H 40/63; G16H 40/20
(Continued)

(56) References Cited

U.S. PATENT DOCUMENTS 5,661,490 A   8/1997 McEwan
5,732,401 A   3/1998 Conway
(Continued)

FOREIGN PATENT DOCUMENTS

CN   1613082 A   5/2005
CN   1856793 A   11/2006
(Continued)

OTHER PUBLICATIONS

European Office Action dated Nov. 26, 2018 for EP Application No. 14173690.0 filed Jun. 24, 2014, 5 pages.
(Continued)

*Primary Examiner* — Emily C Terrell
(74) *Attorney, Agent, or Firm* — Morrison & Foerster LLP

(57) ABSTRACT

A wireless medical room control arrangement includes a wireless controller having a wireless router. A room identifier and a device identifier are stored in the controller. A communication interface sends commands to and receives commands from the wireless controller. In response to commands from the interface, the wireless controller sends wireless control signals to operate medical devices in the room. A room monitor adjacent a doorway provides room identifiers to medical devices and wireless controllers entering the room and provides dummy identifiers to medical devices and controllers exiting the room. The room monitors may connect to a global network processor that determines the location of the medical devices in a medical facility.

23 Claims, 6 Drawing Sheets

Related U.S. Application Data

(60) Provisional application No. 61/129,000, filed on May 27, 2008.

(58) Field of Classification Search
USPC .................. 340/12.22, 539.11, 539.19, 539.1
See application file for complete search history.

(56) References Cited

U.S. PATENT DOCUMENTS

| | | | |
|---|---|---|---|
| 5,788,688 | A | 8/1998 | Bauer et al. |
| 6,581,117 | B1 | 6/2003 | Klein et al. |
| 6,824,539 | B2 | 11/2004 | Novak |
| 6,928,490 | B1 | 8/2005 | Bucholz et al. |
| 7,242,306 | B2 | 7/2007 | Wildman et al. |
| 7,248,933 | B2 | 7/2007 | Wildman |
| 7,289,825 | B2 | 10/2007 | Fors et al. |
| 7,366,934 | B1 | 4/2008 | Narayan et al. |
| 7,463,813 | B2 | 12/2008 | Zwart |
| 7,660,420 | B1 | 2/2010 | Narayan et al. |
| 7,752,050 | B1 | 7/2010 | Hameed et al. |
| 9,740,826 | B2 | 8/2017 | Raghavan |
| 2002/0123687 | A1* | 9/2002 | Birkenbach .......... A61B 5/0002 600/439 |
| 2002/0161317 | A1 | 10/2002 | Risk et al. |
| 2003/0025604 | A1 | 2/2003 | Freeman |
| 2003/0093503 | A1 | 5/2003 | Yamaki et al. |
| 2003/0195644 | A1 | 10/2003 | Borders |
| 2005/0035862 | A1 | 2/2005 | Wildman et al. |
| 2005/0080403 | A1 | 4/2005 | Takahashi |
| 2005/0108057 | A1 | 5/2005 | Cohen et al. |
| 2005/0114170 | A1 | 5/2005 | Park et al. |
| 2005/0251228 | A1 | 11/2005 | Hamel |
| 2006/0116667 | A1 | 6/2006 | Hamel et al. |
| 2006/0165371 | A1 | 7/2006 | Zwart |
| 2006/0255904 | A1 | 11/2006 | Danzer |
| 2007/0080801 | A1 | 4/2007 | Weismiller |
| 2007/0107068 | A1 | 5/2007 | Kelley et al. |
| 2007/0161904 | A1 | 7/2007 | Urbano |
| 2008/0140158 | A1 | 6/2008 | Hamel et al. |
| 2008/0303707 | A1 | 12/2008 | Larsen et al. |
| 2009/0048865 | A1 | 2/2009 | Breazeale |
| 2009/0080348 | A1 | 3/2009 | Hamel et al. |
| 2009/0109033 | A1 | 4/2009 | Salvat |
| 2009/0121865 | A1 | 5/2009 | Hamel et al. |
| 2009/0231124 | A1* | 9/2009 | Klabunde .......... A61B 5/0205 340/539.12 |

FOREIGN PATENT DOCUMENTS

| | | |
|---|---|---|
| EP | 1 432 151 A1 | 6/2004 |
| EP | 1 681 031 A1 | 7/2006 |
| JP | 06-114065 | 4/1994 |
| JP | 2003070805 A | 3/2003 |
| JP | 2006-502779 A | 1/2006 |
| JP | 2008048786 A | 3/2008 |
| KR | 10-2005-0025535 A | 3/2005 |
| WO | WO 2004/093023 A2 | 10/2004 |
| WO | WO 2006/050410 A1 | 5/2006 |
| WO | WO2008033970 A2 | 3/2008 |

OTHER PUBLICATIONS

European Search Report dated Jan. 21, 2015 for EP Application No. 14173685.0 filed on Jun. 24, 2014, 8 pages.
European Search Report dated May 11, 2015 for EP Application No. 14173690.0 filed on Jun. 24, 2014, 10 pages.
Indian Office Action dated Jun. 1, 2018 for IN Application No. 8012/CHENP/2010 filed on Dec. 10, 2010, 6 pages.
Notice of Preliminary Rejection issued by the Korean Patent Office in Appln. No. 10-2010-7026518 with English translation dated Jan. 6, 2016 (11 pages).
Partial European Search Report issued in Appln. No. 14173690.0 dated Jan. 21, 2015 (6 pages).
Japanese Office Action dated Jul. 1, 2013 and English translation (10 pages).
International Preliminary Report on Patentability dated Nov. 30, 2010 for corresponding PCT Application No. PCT/US2009/003128.
International Search Report dated Oct. 29, 2009 (7 pages).
Written Opinion of the International Searching Authority dated Oct. 29, 2009 (14 pages).

* cited by examiner

WIRELESS MEDICAL ROOM CONTROL ARRANGEMENT FOR CONTROL OF A PLURALITY OF MEDICAL DEVICES

CROSS REFERENCE TO RELATED APPLICATIONS

This is a continuation of prior U.S. application Ser. No. 12/454,622, filed May 20, 2009, which claims the benefit of U.S. Provisional Application No. 61/129,000, filed May 27, 2008, both of which are incorporated herein by reference in their entirety.

FIELD OF THE INVENTION

The present invention relates to a system including a wireless controller or control unit for automatically determining the presence of devices within a medical room or other medical area, and for providing central control of the devices without connecting wires and without the need to manually determine which devices are present in the room.

BACKGROUND OF THE INVENTION

Wired central remote control units for controlling medical devices in a medical area, for example, a surgical operating room, have the physical constraint of wired connections to each of the medical devices due to the necessity of using electrical control signal cords. The cords also limit the operating distance of the medical devices from the remote control unit. Eliminating the electrical cords would provide improved accessibility in a medical care area. Further, a medical worker spends a significant amount of time connecting cords between medical devices and a central control unit.

Wired connection to a central controller for some medical devices, such as room lights, along with wall or ceiling mounted cameras, located in a surgical room also is not very practical.

One known operating room control system includes a master controller electrically connected to slave controllers and/or medical devices via a plurality of communication ports. As an alternative, the master controller may be connected to slave controllers or medical devices via wireless communication systems such as IR or RF signal transmitters and receivers on the master controller, slave controllers and medical devices. It is possible that such an operating room control system may actuate a medical device located remotely from the desired working space. This situation may arise when a master controller provides wireless control signals that travel outside of the desired working space and communicate with another surgical device. For example, a master controller may activate a medical device within another adjacent operating room, even when the master controller is located in the correct room or is located in a hallway outside of a nearby operating room.

Accordingly, the present invention encompasses an arrangement that allows a wireless controller to only operate a plurality of devices located in a desired medical room.

A system for preventing unintended activation of a plurality of medical devices or the like according to the invention includes a wireless controller that detects a device identifier for each medical device. The medical devices may be portable or fixedly mounted in a medical room. Further, the wireless controller may be portable or fixedly mounted in a medical room. A room monitor may be provided which communicates a room identifier to medical devices and wireless controllers entering the medical room. In operation, the wireless controller uses the room identifier and device identifiers to identify each medical device in the medical room.

In one embodiment, a global network system receives data from a plurality of room monitors and determines which devices and controllers are located in respective operating rooms. The information can be used to display the type and location of various medical devices in a single room.

Another embodiment enables a user to automatically display at a remote central location the exact number and types of medical devices located in multiple medical rooms, such as patient rooms, operating rooms, storage rooms and nurse stations in a medical facility.

One embodiment prevents a second wireless controller from interfering with control of medical devices by a first wireless controller.

Another embodiment enables wireless central control of portable medical devices and fixed medical devices, such as wall cameras and ceiling mounted lights in a medical room, without requiring wired control connections.

Another embodiment enables wireless control of a plurality of medical devices in a medical room by providing two or more transceiver locator devices in the room for a time-of-flight arrangement that determines the presence of medical devices by their distance from the respective transceiver locator devices. Thus, room identifiers are not required. In some embodiments having a plurality of transceiver locator devices, the exact position of the medical devices in an operating room also may be determined and displayed.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements and in which.

DETAILED DESCRIPTION

Figure 1:
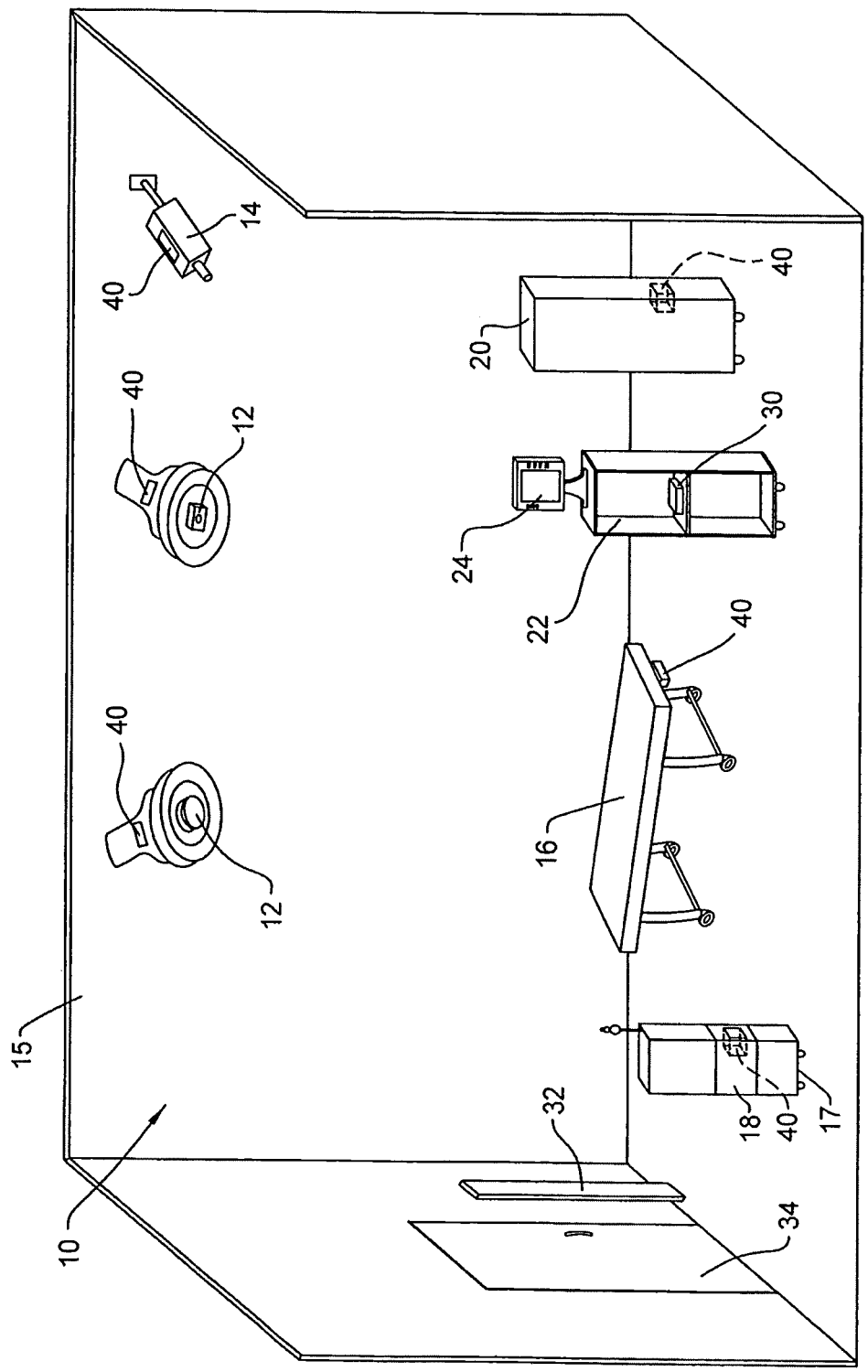
FIG. 1 illustrates a perspective view of an operating room including a central wireless controller for providing output signals to controllable fixed medical devices and to controllable portable medical devices located therein.

FIG. 1 depicts a perspective view of a medical area or room, such as an operating room 10, according to one embodiment of the present invention. The operating room 10 includes operating room lights 12 and a camera 14 mounted to one of the ceiling, a room wall 15 or other stationary structure. The operating room 10 further includes a surgical table 16, a movable cart 17 supporting an arthroscopic pump system 18 and a portable waste management system 20. As shown in FIG. 1, a further movable cart 22 carries a communication interface, such as a portable touch screen wireless tablet 24, along with a central wireless controller 30 for controlling the various medical devices 12, 14, 16, 18, 20 in the operating room 10.

It will be appreciated that in some embodiments the wireless controller 30 is intended to remain in the room and thus need not be provided on a cart 22.

FIG. 1 further illustrates a room monitor 32 located adjacent a door or entryway 34. The room monitor 32 only communicates with medical devices 16, 18, 20, 24 and controllers 30 entering or exiting the room 10.

Figure 2:
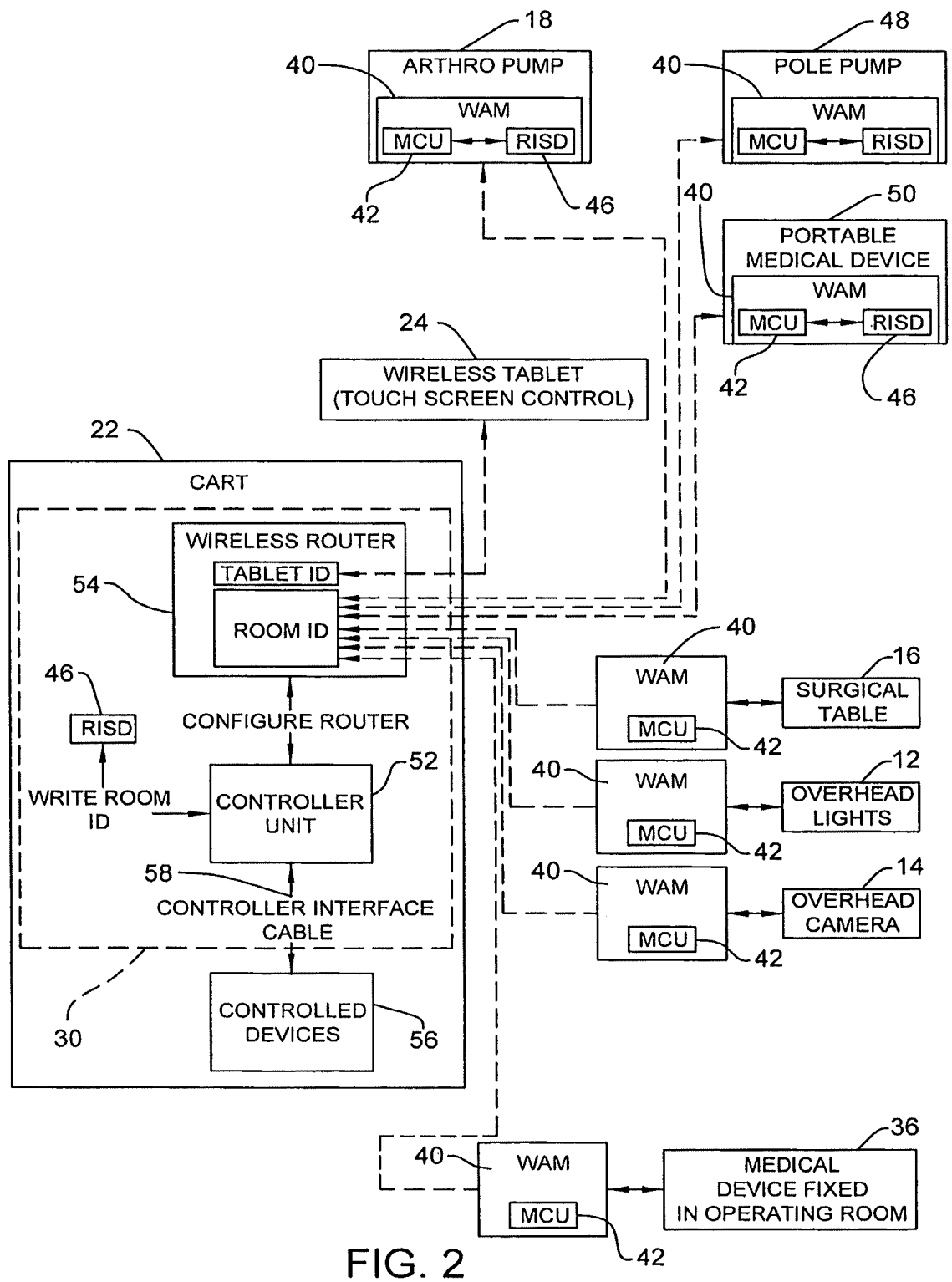
FIG. 2 is a block diagram of a system for use in a medical room including a cart supporting a central wireless controller, according to a first embodiment of the invention.

The embodiment of FIG. 2 shows each fixed medical device 12, 14, 16 in the operating room and a fixed medical device 36 fixedly mounted in the operating room. The medical device 36 is intended to represent any type of known fixed medical device, including the fixed medical devices 12, 14, 16, that may be provided in an operating room 10. Each fixed medical device 36 includes a wireless adapter module (WAM) 40 having a micro-controller unit (MCU) 42.

FIG. 2 also illustrates the arthroscopic pump system 18 provided on the cart 17 shown in FIG. 1, along with a portable pole pump system 48, and a portable medical device 50. The portable medical device 50 is intended to represent any type of portable medical device that may be provided in an operating room, including portable devices 18, 20, 48. Each portable medical device 50 includes a wireless adapter module (WAM) 40. The wireless adapter module (WAM) 40 includes both a micro controller unit (MCU) 42 and a room identifier storage device (RISD) 46.

In FIG. 2, the central wireless controller 30 is a portable central wireless controller represented by broken line. The wireless controller 30 includes a controller unit 52 connected to a wireless router 54. Since the wireless controller 30 is portable, a room identifier storage device (RISD) 46 is provided therewith. The controller unit 52 and/or the wireless router 54 stores a unique tablet/controller identifier that corresponds to a unique tablet/controller identifier stored in the wireless tablet 24. The wireless router 54 further receives a room identifier from the controller unit 52 that corresponds to a room identifier stored in the room identifier storage devices 46 of the portable medical devices 50 located in the medical room 10. The same room identifier is also, in one embodiment, permanently stored in the microcontroller units 42 of the wireless adapter modules 40 of the fixedly mounted medical devices 36 located in the operating room 10.

Since the fixedly mounted medical devices 36, such as the overhead lights 12, overhead camera 14, and surgical table 16, have the room identifier stored in the micro controller unit 42 thereof, these devices do not require a room identifier storage device (RISD) 46 although one may be provided.

In some embodiments, the portable cart 22 supports additional controlled devices 56 thereon that connect to the controller unit 52 by a conventional interface cable 58.

Figure 3:
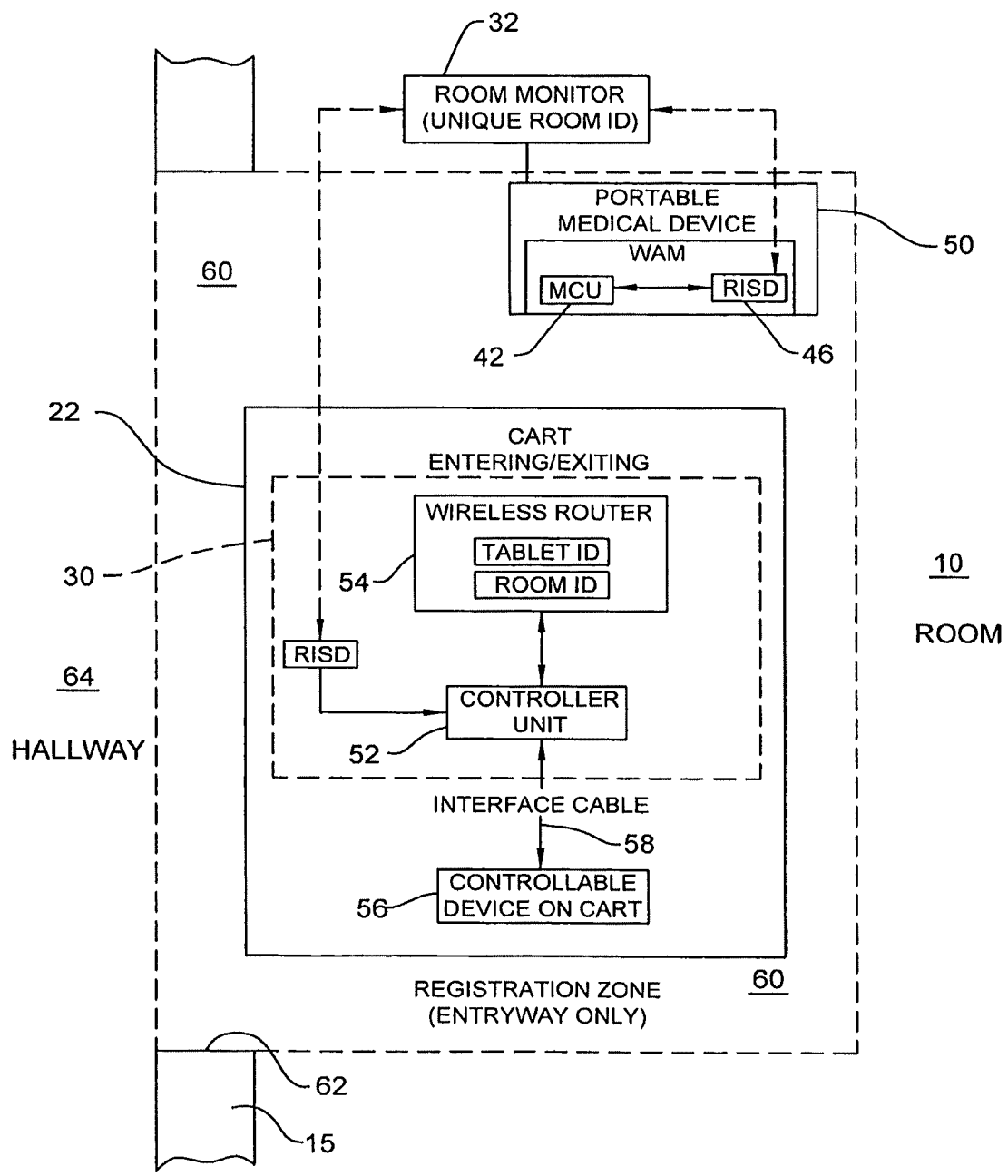
FIG. 3 is a block diagram illustrating passage of a portable central controller and a portable medical device through a registration zone of a room monitor located near a door of an operating room.

The embodiment of FIG. 3 is a block diagram showing the room monitor 32 having a registration zone 60 in the operating room 10 adjacent a doorway 62 connecting the room to a hallway 64. In FIG. 3, the hallway 64 in the medical facility is oriented to the left of the room monitor 32.

FIG. 3 also illustrates both a portable cart 22 with a central wireless controller 30 and a portable medical device 50 located within the registration zone 60 of the room monitor 32. The cart 22 and medical device 50 are either entering or exiting the operating room 10.

Operation

In one embodiment, the room monitor 32 and at least one of the portable medical devices 50 and/or the central wireless controller 30 on the cart 22 enter into the room 10 through the open doorway 62. The room monitor 32 senses entry of the portable medical device 50 and of the controller 30. The room monitor 32 then sends a room identifier for storage in the room identifier storage device 46 of the portable medical device 50 and of the portable wireless controller 30 that are passing through the registration zone 60 and into the room 10. Thus, when the portable controller 30 enters the operating room 10, the controller 30 and each of the fixed or portable operating room devices 36, 50 in the room have the same room identifier stored therein. This arrangement will be discussed in more detail later herein.

To enable operation of the respective devices 36, 50 when the wireless controller 30 is powered, the controller unit 52 reads the room identifier stored in the room identifier storage device 46 and provides the room identifier to the wireless router 54.

The wireless controller 30 utilizes the room identifier and wireless router 54 to determine which fixed and portable controllable medical devices 36, 50 are located in the operating room 10. The determination results from the wireless router 54 sending the room identifier along with device identifiers that correspond to individual devices 36, 50 and then waiting for a reply. The medical devices 36, 50 then return a wireless signal including the room identifier and a device identifier so that the central controller 30 is aware of the types of medical devices in the operating room 10. This polling operation occurs automatically without prompting by an operator at start up as the wireless router 54 sends consecutive signals with the room identifier and different device identifiers and detects replies from the different devices in the room 10. Automatic updates of the medical devices 36, 50 in the operating room 10 occur periodically.

In operation, in one embodiment a user touches the touch screen of the wireless tablet 24, which sends the tablet/controller identifier and a device identifier, along with information and control commands, to the wireless router 54. The wireless router 54 reads the tablet/controller identifier sent from the tablet 24. A comparison of the tablet/controller identifier prevents the transfer or communication of commands from a different tablet not associated with the wireless controller 30. The wireless router 54 forwards the control commands and identifiers to the controller unit 52. The controller unit 52 then determines if the commands are proper and what the control commands are. Control commands, along with the room identifier and the device identifier, are then sent from the controller unit 52 to the wireless router 54. The wireless router 54 transmits wireless signals that include the identifiers and commands to the medical device 36, 50 to be controlled. The appropriate wireless adapter module 40 matches the room identifier and the device identifier for the medical device connected thereto, and the commands are then executed. Thus, the command from the tablet 24 is wirelessly transferred to the controller unit 52 and then wirelessly transferred to the selected medical device 36, 50.

The selected medical device 36, 50 being controlled may also return device data or information to the central wireless controller 30. The device identifier stored in the microcontroller unit (MCU) 42 of the wireless adapter module 40 is wirelessly transmitted with return commands or information that is received by the wireless router 54 and forwarded to the controller unit 52. The controller unit 52 processes the commands or information and sends relevant information, including the unique tablet/controller identifier, via the wireless router 54 to the tablet 24 for display of the medical device information on the touch screen.

In some embodiments, the controller unit 52 also controls a controlled device 56 mounted on the cart 22 via the conventional wired interface cable 58. In this arrangement, the central controller 30 does not require a wireless connection, much less a room identifier, to operate the controllable medical device 56. Therefore, the controlled medical device 56 does not require a wireless adapter module 40.

Entry/Exit from Operating Room

When the wireless controller 30 on the portable cart 22 exits the operating room 10, the room monitor 32 detects the exiting of the controller. In response to the detection, the room monitor 32 transmits a dummy identifier that overwrites the identifier stored in the room identifier storage device (RISD) 46. Thus, upon exit from the operating room 10 and entering the hallway 64, the central wireless controller 30 is inhibited from wirelessly controlling any medical devices 36, 50 in any of the nearby operating rooms 10 of a medical facility. Likewise, any of the portable medical devices 50 exiting room 10 is provided with a dummy identifier that prevents operation of the medical device in response to a control signal from a wireless controller 30 located at any nearby location.

With regard to the portable medical devices 50 entering or exiting the operating room 10 through the registration zone 60, the respective room identifier or dummy identifier is stored in the room identifier storage device (RISD) 46 even if the medical device 50 is not powered. For example, after an unpowered portable medical device 50 enters room 10 and is later powered up, the room identifier is read by the MCU 42 of the wireless adapter module 40.

Likewise, if the wireless controller 30 moves unpowered into the operating room 10 through the registration zone 60, the room identifier is stored in the room identifier storage device 46. When the central wireless controller 30 is later powered up, the controller unit 52 receives the room identifier from the room identifier storage device 46 and sends the room identifier to the wireless router 54 to begin communicating with and automatically polling all of the medical devices 36, 50 in the room that are powered on and have the correct room identifier.

In another embodiment, when an unpowered wireless controller 30 on a cart 22 exits the doorway 62 through the registration zone 60, the room identifier storage device (RISD) 46 thereon receives the dummy identifier from the room monitor 32. Later, when the wireless controller 30 is powered on, the dummy identifier is configured by the controller unit 52 and sent to the wireless router 54 to prevent the router, and thus the wireless controller 30, from communicating with any medical device. Thus, outside of the operating room 10, the central wireless controller 30 is only capable of controlling medical devices 56 that are directly wired thereto through the interface cable 58.

In another embodiment, first and second central wireless controllers 30 may be located in the same operating room 10. For instance, in one situation a first central wireless controller 30 is located in an operating room 10 and the medical devices 36, 50 in the room are wirelessly connected thereto and ready for user control. An unpowered second central wireless controller 30 then passes through the registration zone 60 of the room monitor 32 and enters the room. In this embodiment, the room monitor 32 is provided with memory which stores the types of controllable portable medical devices 50 in the room and whether a wireless controller 30 is already located in the operating room 10. Since the room monitor 32 recognizes that a first wireless controller 30 is already present within the operating room 10, the room monitor 32 writes a control disable identifier to the room identifier storage device (RISD) 46 of the second central wireless controller 30 entering the room.

When the second wireless controller 30 within the room 10 is plugged into a power supply and powered up, the wireless controller unit 52 of the second wireless controller 30 receives the disable identifier from the room identifier storage device (RISD) 46. The second wireless controller 30 is configured with the disable identifier to prevent communication with the controllable medical devices 36, 50. The control unit 52 reads the disable identifier of the second wireless controller 30 and provides an error message through the wireless router 54 thereof to the tablet 24 indicating that multiple wireless controllers 30 are located in the medical room 10 and that the second central wireless controller is disabled.

When the second wireless controller 30 is subsequently removed from the operating room 10, the room monitor 32 removes the disable identifier and provides a different dummy identifier therein. Thus, the second wireless controller is again available for use upon entry into any other operating room 10.

During the entire time of the entry and exit of the second non-enabled wireless controller 30 from the operating room 10, the first central wireless controller 30 functions in a normal manner.

In another embodiment, a second central wireless controller 30 enters an operating room 10 having a first wireless controller 30 and receives a disable identifier as discussed above. The first wireless controller 30 is removed from the operating room 10. The first wireless controller 30 is unregistered and receives a dummy identifier from the room monitor 32. Then, as expected and desired, the first wireless controller 30 is unable to control medical devices 36, 50 from the hallway 64. The second central wireless controller 30 that remains in the operating room 10, however, remains in a disabled state and as discussed above, is unavailable for use. To override the disabled state, a user must remove the second central wireless controller 30 from the operating room 10 and return the second controller 30 to the room so that the second controller 30 obtains the room identifier and functions normally to wirelessly control the portable devices 50 along with the fixed medical devices 36 located in the operating room.

In another embodiment, the disable identifier includes the room identifier in a form not recognizable by the second controller 30. Since the disable identifier differs from a dummy identifier, the second controller 30 recognizes that it is located in an operating room 10. A user then has the option of actuating the second central wireless controller 30 through an interface, such as the touchscreen tablet 24 to enable the second wireless controller 30 to obtain the room identifier stored within the disable identifier. Then the second wireless controller 30 is operable to control the medical devices 36, 50 within the operating room 10.

In another embodiment, two or more central wireless controllers 30 enter an operating room at essentially the same time. For instance, both central wireless controllers 30 are on the same portable cart 22. The first wireless controller 30 that is detected by the room monitor 32 is provided with the room identifier and operates to wirelessly control the medical devices 36, 50 in a normal manner. The second detected central wireless controller 30, however, will be provided with a disable identifier. The controllers 30 then operate in the manner as discussed above.

In other embodiments, multiple medical devices 36, 50 of the same type, such as two viewing cameras, are located in the same operating room 10. In one embodiment, the detected presence of multiple medical devices of the same type having the same device identifier is not allowed and a duplicate device warning message is provided to the tablet 24 by the central wireless controller 30. The one of the multiple medical devices 36, 50 that first connects wirelessly to the controller unit 52 of the wireless controller 30 through the wireless router 54 is available for control by the central wireless controller 30. The other duplicate medical device, however, will be ignored and not wirelessly operable.

In some embodiments, the second non-enabled medical device 36, 50 is connected and then the enabled identical medical device is disconnected. The second medical device 36, 50 will then be enabled for use and control by the wireless controller 30.

In embodiments including, for example, two different room lights 12 provided in an operating room 10, the room lights each have a specific different device identifier. Thus, the room lights 12 may be capable of separate operation or combined operation depending on the commands sent thereto from the wireless controller 30.

In some embodiments, the wireless router 54 is provided with two different tablet/controller identifiers that correspond to different tablets so that two tablets are capable of controlling devices through a single wireless controller 30.

In various embodiments, the room monitor 32 is designated as a sensing and communication system for communicating with room identifier storage devices (RISD) 46 that are RFID elements. In other embodiments, different types of known communication or memory storage devices 46 may be utilized. For example, infrared and ultrasonic signals are usable in place of radio frequency signals to provide room identifiers or data signals to a room identifier storage device 46 entering or exiting the operating room 10.

In another embodiment, the registration zone 60 of the room monitor 32 comprises a pair of adjacent zones extending across the doorway 64. A first zone at the doorway 62 provides the dummy identifier. The second zone in the operating room 10 and adjacent to the first zone provides a room identifier to medical devices 50 entering the room. In this embodiment, the room monitor 30 does not read any identification data from the medical devices 50 in the registration zone 60. Portable wireless controllers 30 entering or exiting the operating room 10 through the registration zone 60 are provided with identifiers in the same manner.

The wireless adapter modules 40 are illustrated as being separate external elements connected to the respective fixed medical devices 36. In FIG. 2, the wireless adapter modules 40 are shown located internally within the housing of the respective medical devices 50. It will be appreciated that either arrangement is acceptable for any given medical device 36, 50.

While the above discussion is mainly directed to embodiments of a portable central wireless controller 30 provided on a portable cart 22 in combination with other medical devices, such as pump system 18 and pole pump 48 that are mounted on a cart 17 or movable stand, the same operation is possible for other types of medical or surgical devices that are provided with a wireless adapter module 40 as represented by devices 36, 50. Such surgical devices may include shavers, endoscopic cameras, cutting tools, drills, and other powered equipment utilized in medical or surgical procedures.

While the above embodiments disclose the use of a wireless touch screen tablet 24 for the communication interface, in other embodiments the communication interface may be connected to the wireless controller 30 by a cable. Thus, a tablet identifier would not be necessary.

In some embodiments, the communication interface is a video screen for displaying information and a separate control keyboard connected to the controller 30. In other embodiments, a voice interface provides voice commands that are translated by a voice recognition device and utilized to control the medical devices 36, 50 in the operating room 10 through the central wireless controller 30.

While the above embodiments generally involve the use of a room identifier and a device identifier, further unique identifiers can be provided indicating the specific medical device 36, 50 in the operating room 10. For example, in addition to a device identifier, a specific manufacturer model registration code can be provided so that the room monitor 32 identifies not only the type of medical device, but the exact medical device. This enables data on the history of use or locations of the device to be stored as discussed later herein. Further, multiple medical devices 36, 50 of the same type can be separately identified and controlled in an operating room 10.

While the above described embodiments include the central wireless controller 30 as a portable or mobile device, in some embodiments the central wireless controller 30 may be a permanent structure fixed within the operating room 10 or intended to remain in the operating room. In these embodiments, the central wireless controller 30 does not require a room identifier storage device (RISD) 46, but instead has the room identifier stored in the controller unit 52 and/or the wireless router 54. The stored identifier corresponds to the room identifier provided in the room monitor 32 for the operating room 10. Otherwise, the fixed wireless controller 30 operates in the same manner as the cart-based or portable central wireless controller 30 discussed above.

Time of Flight Arrangement

Figure 4:
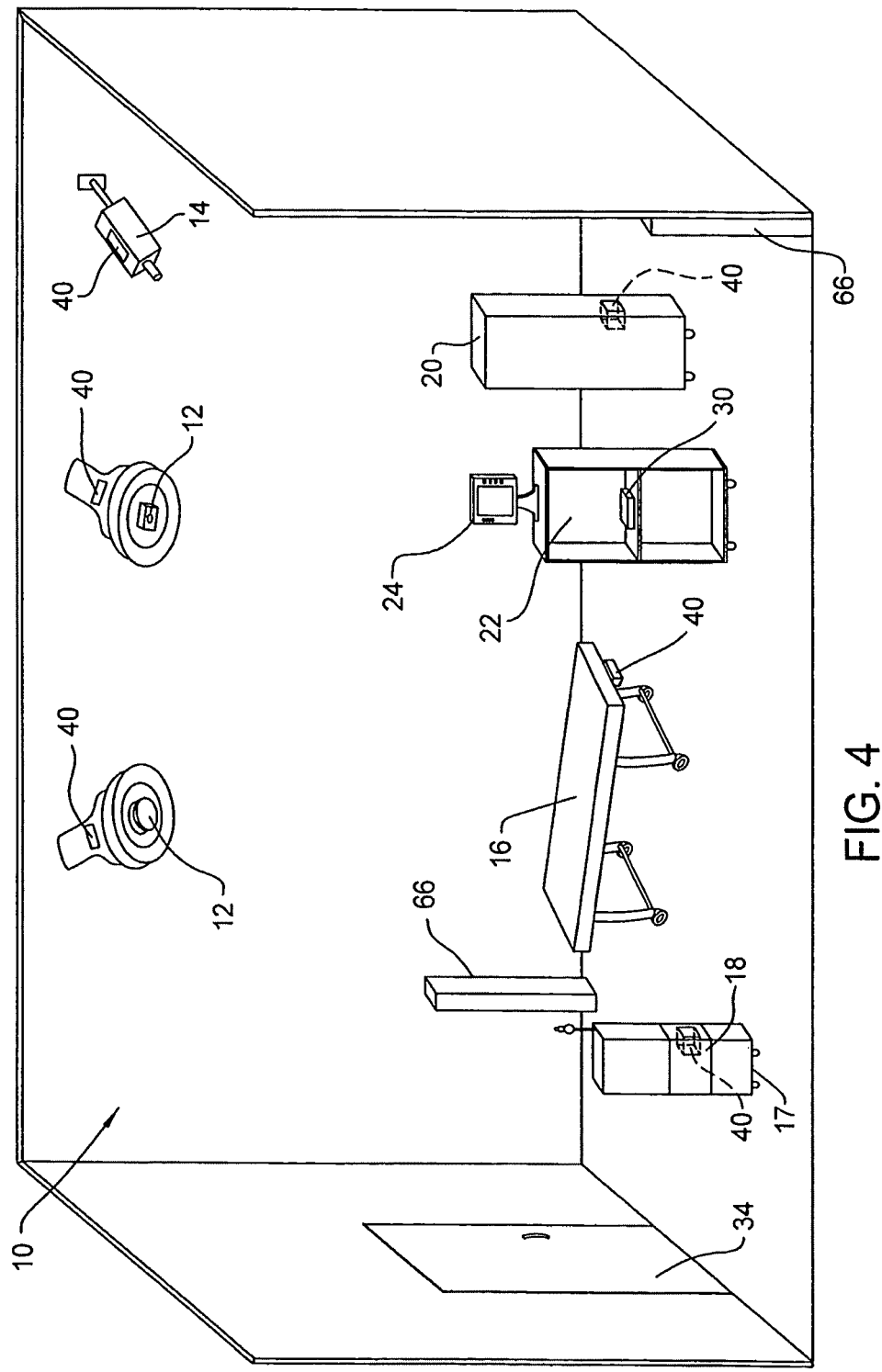
FIG. 4 illustrates a perspective view of an operating room having transceiver locator identifier devices to determine the presence of controllable medical devices in the operating room.

FIG. 4 illustrates a "time-of-flight" arrangement for a central wireless controller 30 that is fixedly located in a operating room 10 in most embodiments. Elements in FIG. 4 having the same reference numerals as in the arrangements shown in FIGS. 1-3 represent the same element or device.

The main difference in the embodiment of FIG. 4 with respect to the earlier described embodiments is the absence of a room monitor 32 located adjacent the door 34 of the operating room 10. Instead, the central controller 30 relies on two or more transceiver locator devices 66, and for example at least five transceiver locator devices, provided within the operating room 10 to determine the presence of fixed medical devices 36 and portable medical devices 50 located in the room.

The time of flight embodiment with multiple transceiver locator devices 66 shown in FIG. 4 provides separate distance values from each of the respective locator devices 66 to each medical device 36, 50 by, for example, timing the sending of a specific signal to the specific device and determining the return time of a return signal including a unique device identifier. In one embodiment this information is then sent wirelessly to the wireless controller 30. The wireless controller 30 compiles the distance values for each device from the multiple transceiver locator devices 66 to determine the exact location for each fixed or portable medical device 36, 50 in the operating room 10. In some embodiments, the locations are displayed on a room map provided on a display screen or on the tablet 24. The central controller 30 then wirelessly controls the identified medical devices 36, 50 located in the operating room 10 as discussed above.

While the embodiment of FIG. 4 shows two transceiver locator devices 66 capable of identifying the presence of medical devices 36, 50 within the medical room 10, in another embodiment a fixed transceiver locator device 66 is mounted on each wall, along with the floor and ceiling. In this embodiment, the six transceiver locator devices 66 each measure respective distances thereto from each medical device 36, 50 and the controller 30. The measured distances of each medical device 36, 50 from each of the six transceiver locator devices 66 are correlated to determine whether the respective medical device is in the operating room 10 and available for use. Further, the exact locations of the devices 36, 50 and the controller 30 are determined by a central time-of-flight microcomputer or the like. These locations are provided to the wireless controller 30 for display on a room map provided on a monitor, display screen, or a tablet. The map enables a user to easily locate the devices 36, 50 in the operating room.

In another embodiment, the time-of-flight location system operates to detect the presence of devices in the operating room 10 according to the system disclosed in U.S. Pat. No. 5,661,490, the disclosure of which is hereby incorporated by reference in its entirety.

In one embodiment of the above time-of-flight arrangement, the portable devices 36 do not require a room identifier storage device (RISD) 46 for storing a room identifier. Instead, each portable or fixed medical device 36, 50 only receives transmissions from transceiver locator devices 66 and returns signals with a unique device identifier.

Further, the above time-of-flight embodiments do not require room monitors 32, much less room monitors with memory to remember the portable controllers 30 and portable medical devices 50 located in an operating room 10.

In most embodiments, the unique device identifier that identifies the exact individual medical device 36, 50 is a stored model registration number.

Global Network System

Figure 5:
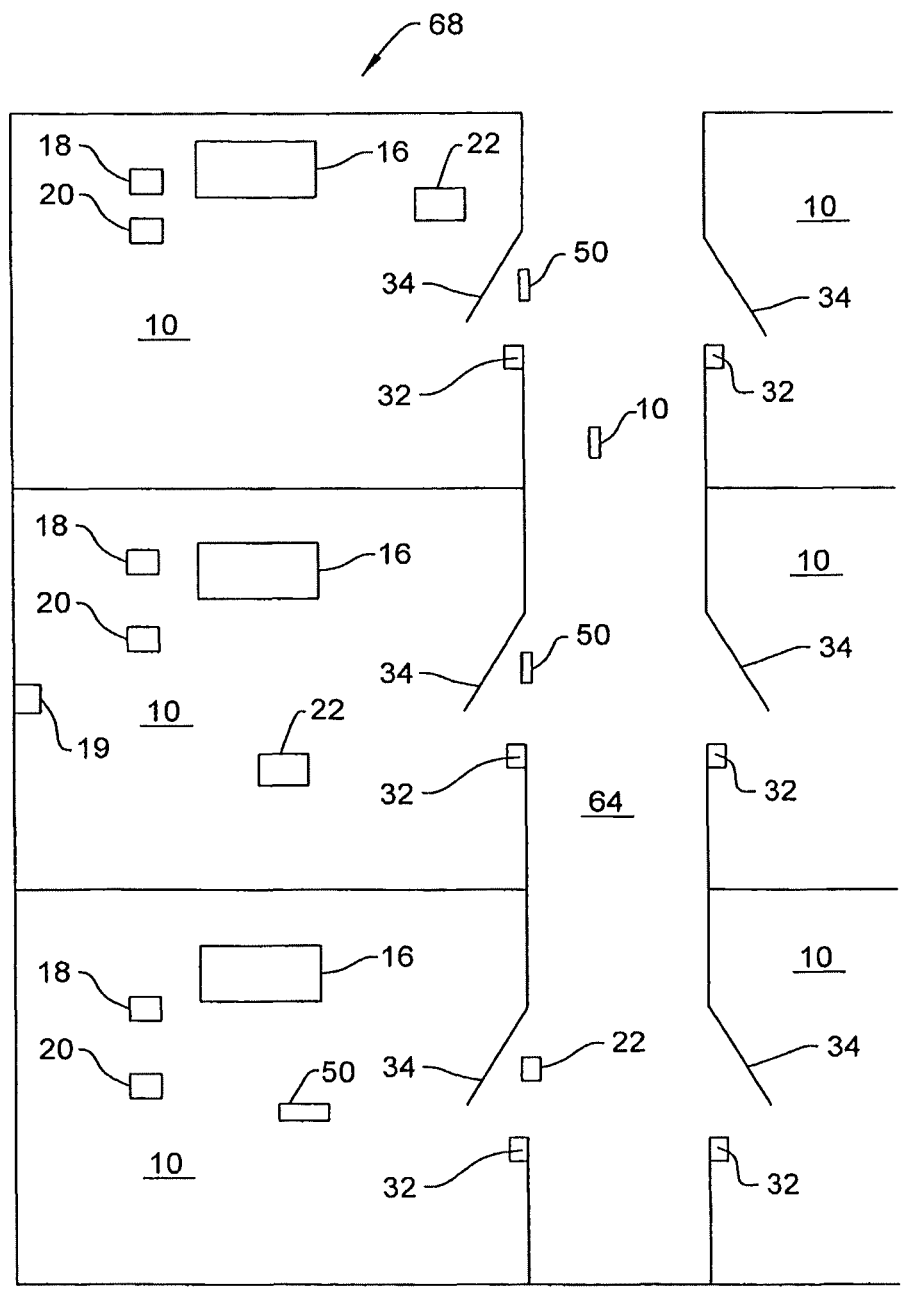
FIG. 5 is a diagrammatical block diagram of a medical facility or building showing the arrangement of a global network system in a surgical operating room according to another embodiment of the invention.
Figure 6:
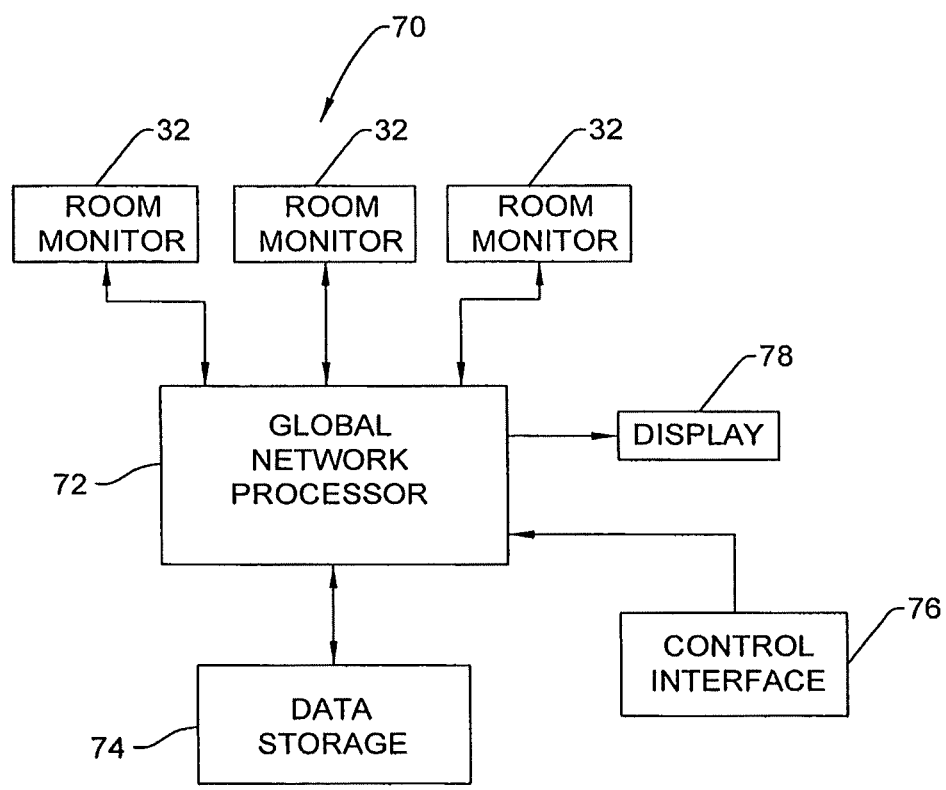
FIG. 6 illustrates a partial diagram of a medical facility showing a global network system that provides outputs to a global network processing system according to another embodiment of the invention.

FIGS. 5 and 6 illustrate a global network system that detects various devices in a room. Another arrangement for a global network system for a foot controller is disclosed in U.S. Provisional Application No. 60/995,330, owned by the Assignee hereof and filed Sep. 26, 2007, the disclosure of which is hereby incorporated by reference in its entirety.

The partial diagram of a medical facility 68 illustrated in FIG. 5 includes a hallway 64 and a plurality of medical rooms 10. The medical rooms 10 include operating rooms and storage rooms. The individual operating rooms 10 may have surgical tables 16 and other systems and medical devices 36, 50 represented by the same reference numerals as described above with respect to the earlier embodiments.

FIG. 6 depicts a block diagram of a global network system 70 according to one embodiment of the present invention. The global network system 70 includes a global network processor 72, data storage 74, a control interface 76 connected to the global network processor 72 and a display 78. The control interface 76 and display 78 are provided at a remote location.

As discussed above, in earlier embodiments, the room monitors 32 detect the exiting and entering of portable central wireless controllers 30 and portable medical devices 50 from the respective operating rooms 10. In this embodiment the detected information is stored in the room monitor 32. The detected information may include device data for the medical devices 36, 50 in the respective operating room 10, along with unique device identifiers.

The global network processor 70 receives outputs from each of the room monitors 32. In one embodiment, the global network system 70 determines if the portable medical devices 50 and portable wireless controllers 30 are located in a particular operating room 10 to ensure that the necessary medical devices are present therein for a particular type of scheduled surgery. The medical devices in the operating room 10 are listed on display 78.

In some embodiments, the room monitors 32 not only determine the respective operating rooms 10 within a medical building or facility 68 having medical devices 50 and portable wireless controllers 30 located therein, but also sense unique identifiers for each of the portable medical devices 50 and the portable central wireless controllers 30. The unique identifiers enable recording of the location, history or usage of each specific portable medical device 50 and each portable controller 30, along with any other relevant data. The location data for all of the portable medical devices 50 and the respective central wireless controllers 30 is received from the room monitors 32 by the global network processor 72. The global network processor 72 compiles the data and stores the data in data storage 74.

In another embodiment, the data storage 74 stores additional data and other information for each specific medical device 36, 50, such as whether the medical device is sterilized. Again, this data is first received by the global network processor 72 from the respective room monitors 32. In response to an input at the control interface 76, the display 78 shows the exact portable medical devices 50 and their locations to assist in collection of the medical devices for servicing.

In another embodiment, separate storage rooms also have room monitors 32. This arrangement enables the global network system 70 to provide an inventory of portable medical devices 50 and portable wireless controllers 30, including their locations in medical rooms, storage rooms, patient rooms and elsewhere throughout the facility.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense.

What is claimed is:

1. A wireless control arrangement for a medical room comprising:
   at least one controllable portable medical device located in the medical room, the at least one controllable portable medical device including a room identifier identifying the medical room and a device identifier stored therein;
   a wireless controller located in the medical room, the wireless controller including a room identifier identifying the medical room and a device identifier stored therein;
   wherein the arrangement automatically determines the medical device located in the medical room; and
   wherein the wireless controller sends wireless control commands recognized by the at least one controllable portable medical device located in the medical room to operate the at least one controllable portable medical device.

2. The wireless control arrangement of claim 1, wherein:
   the wireless controller located in the medical room transmits the room identifier to the at least one controllable portable medical device to automatically determine that the at least one controllable portable medical device is located in the medical room, the wireless controller being portable.

3. The wireless control arrangement of claim 1, further including:
   a communication interface for providing control commands to the wireless controller.

4. The wireless control arrangement of claim 3, wherein:
   the wireless controller provides the at least one controllable portable medical device to the communication interface for display thereon.

5. The wireless control arrangement of claim 1, further including:
   a room monitor disposed adjacent a doorway for monitoring the at least one controllable portable medical device entering and exiting the medical room, the room monitor having the room identifier and a dummy identifier stored therein;
   wherein the at least one controllable portable medical device includes a room identifier storage device;
   wherein the wireless controller includes a room identifier storage device, wherein the room monitor senses entry of the at least one controllable portable medical device in a powered or unpowered state and the wireless controller in a powered or unpowered state into the medical room and wirelessly provides the room identifier to the at least one controllable portable medical device entering the medical room and the wireless controller entering the medical room for storage in the respective room identifier storage device; and
   wherein the room monitor senses exit of the at least one controllable portable medical device in the powered or unpowered state and the wireless controller in the powered or unpowered state from the medical room and wirelessly provides the dummy identifier to the at least one controllable portable medical device exiting the medical room in the powered or unpowered state and the wireless controller exiting the medical room in the powered or unpowered state to prevent unintended operation thereof.

6. The wireless control arrangement of claim 1, wherein:
   the device identifier of the at least one controllable portable medical device comprises a unique device identifier so that the wireless controller automatically identifies the at least one controllable portable medical device; and
   the unique device identifier enables control of the at least one controllable portable medical device in the medical room.

7. The wireless control arrangement of claim 1, further including:
   at least two transceiver locator devices provided in the medical room for sensing the device identifier stored in the at least one controllable portable medical device located in the medical room to determine a presence and location of the at least one controllable portable medical device, and for notifying the wireless controller of the at least one controllable portable medical device located in the medical room.

8. The wireless control arrangement of claim 7, wherein:
   the at least two transceiver locator devices comprise time-of-flight devices for determining the presence and location of the at least one controllable portable medical device in the medical room depending on time-of-flight signals.

9. The wireless control arrangement of claim 1, wherein:
   the at least one controllable portable medical device comprises at least one of operating room lights, operating room cameras, a pole pump system, an arthroscopic pump system and a waste management system.

10. A wireless control arrangement for a medical room comprising:
    a medical device located in the medical room, the medical device including a room identifier stored therein;
    a wireless controller located in the medical room, the wireless controller including a room identifier stored therein;
    wherein the wireless controller sends control commands that include the room identifier to the medical device to operate the medical device; and
    wherein the room identifier prevents the wireless controller from controlling a medical device located in an area other than the medical room.

11. The wireless control arrangement of claim 10, wherein:
    the wireless controller located in the medical room transmits the room identifier to the medical device to automatically determine that the controllable medical device is located in the medical room, the wireless controller being portable.

12. The wireless control arrangement of claim 10, further including:
    a communication interface for providing control commands to the wireless controller.

13. The wireless control arrangement of claim 12, wherein:
    the wireless controller provides the medical device to the communication interface for display thereon.

14. The wireless control arrangement of claim 10, further including:
    a room monitor disposed adjacent a doorway for monitoring the medical device entering and exiting the medical room, the room monitor having the room identifier and a dummy identifier stored therein;
    wherein the medical device includes a room identifier storage device;
    wherein the wireless controller includes a room identifier storage device, wherein the room monitor senses entry of the medical device in a powered or unpowered state and the wireless controller in a powered or unpowered state into the medical room and wirelessly provides the room identifier to the medical device entering the medical room and the wireless controller entering the medical room for storage in the respective room identifier storage device; and wherein the room monitor senses exit of the medical device in the powered or unpowered state and the wireless controller in the powered or unpowered state from the medical room and wirelessly provides the dummy identifier to the medical device exiting the medical room in the powered or unpowered state and the wireless controller exiting the medical room in the powered or unpowered state to prevent unintended operation thereof.

15. The wireless control arrangement of claim 10, wherein:

at least one controllable portable medical device includes a device identifier stored therein; and the wireless controller includes a device identifier stored therein.

16. The wireless control arrangement of claim 15, wherein:

the device identifier of the at least one controllable portable medical device comprises a unique device identifier so that the wireless controller automatically identifies the at least one controllable portable medical device; and the unique device identifier enables control of the at least one controllable portable medical device in the medical room.

17. The wireless control arrangement of claim 15, further including:

at least two transceiver locator devices provided in the medical room for sensing the device identifier stored in the at least one controllable portable medical device located in the medical room to determine a presence and location of the at least one controllable portable medical device, and for notifying the wireless controller of the at least one controllable portable medical device located in the medical room.

18. The wireless control arrangement of claim 17, wherein:

The at least two transceiver locator devices comprise time-of-flight devices for determining the presence and location of the at least one controllable portable medical device in the medical room depending on time-of-flight signals.

19. The wireless control arrangement of claim 10, wherein:

the at least one controllable portable medical device comprises at least one of operating room lights, operating room cameras, a pole pump system, an arthroscopic pump system and a waste management system.

20. A wireless control arrangement for a medical room comprising:

at least one controllable portable medical device located in the medical room, the at least one controllable portable medical device including a device room identifier storage device;

a room monitor disposed adjacent a doorway for monitoring the at least one controllable portable medical device entering and exiting the medical room, the room monitor having a room identifier and a dummy identifier stored therein;

a portable wireless controller including a controller room identifier storage device;

wherein the room monitor senses entry of the powered or unpowered portable medical device and the powered or unpowered portable wireless controller into the medical room and wirelessly provides the room identifier to the entering portable medical device and the entering portable wireless controller for storage in the respective room identifier storage device; and wherein the room monitor senses exit of a powered or unpowered the portable medical device and a powered or unpowered the portable wireless controller from the medical room and wirelessly provides the dummy identifier to the powered or unpowered exiting portable medical device and the powered or unpowered exiting wireless controller to prevent unintended operation thereof.

21. The wireless control arrangement of claim 20, wherein:

the wireless controller located in the medical room transmits the room identifier to the at least one controllable portable medical device to automatically determine that the at least one controllable portable medical device is located in the medical room, the wireless controller being portable.

22. The wireless control arrangement of claim 20, further including:

a communication interface for providing control commands to the wireless controller.

23. The wireless control arrangement of claim 22, wherein:

the wireless controller provides the at least one controllable portable medical device to the communication interface for display thereon.

* * * * *